United States Patent
Artof et al.

(10) Patent No.: US 6,830,585 B1
(45) Date of Patent: Dec. 14, 2004

(54) PERCUTANEOUSLY DELIVERABLE HEART VALVE AND METHODS OF IMPLANTATION

(75) Inventors: Jason Artof, Newport Beach, CA (US); Rodolfo C. Quijano, Laguna Hills, CA (US); Hosheng Tu, Newport Beach, CA (US)

(73) Assignee: 3F Therapeutics, Inc., Lake Forest, CA (US)

(*) Notice: Subject to any disclaimer, the term of this patent is extended or adjusted under 35 U.S.C. 154(b) by 0 days.

(21) Appl. No.: 10/342,093

(22) Filed: Jan. 14, 2003

(51) Int. Cl.[7] .................................................. A61F 2/24
(52) U.S. Cl. ...................................... 623/2.11; 623/904
(58) Field of Search ............................ 623/2.1–21.9, 623/904

(56) References Cited

U.S. PATENT DOCUMENTS

| | | | | |
|---|---|---|---|---|
| 5,156,621 A | * | 10/1992 | Navia et al. ............... 623/2.12 |
| 5,411,552 A | | 5/1995 | Andersen et al. |
| 5,713,953 A | * | 2/1998 | Vallana et al. ............. 623/2.15 |
| 5,840,081 A | | 11/1998 | Andersen et al. |
| 6,168,614 B1 | | 1/2001 | Andersen et al. |
| 6,203,553 B1 | | 3/2001 | Robertson et al. |
| 6,241,765 B1 | * | 6/2001 | Griffin et al. ............. 623/2.38 |
| 6,270,526 B1 | | 8/2001 | Cox |
| 6,283,127 B1 | | 9/2001 | Sterman et al. |
| 6,371,983 B1 | * | 4/2002 | Lane ......................... 623/2.14 |
| 6,425,916 B1 | | 7/2002 | Garrison et al. |
| 6,540,781 B2 | * | 4/2003 | Adams ....................... 623/2.13 |
| 6,558,417 B2 | * | 5/2003 | Peredo ....................... 623/2.13 |
| 6,569,196 B1 | * | 5/2003 | Vesely ........................ 623/2.14 |
| 6,613,087 B1 | * | 9/2003 | Healy et al. ............... 623/2.14 |
| 2001/0007956 A1 | | 7/2001 | Letac et al. |
| 2001/0010017 A1 | | 7/2001 | Letac et al. |
| 2002/0052651 A1 | | 5/2002 | Myers et al. |
| 2002/0094573 A1 | * | 7/2002 | Bell ............................ 435/398 |
| 2002/0165609 A1 | * | 11/2002 | Cox .......................... 623/2.12 |
| 2002/0198594 A1 | * | 12/2002 | Schreck ..................... 623/2.11 |
| 2003/0069635 A1 | * | 4/2003 | Cartledge et al. .......... 623/2.13 |
| 2003/0125793 A1 | * | 7/2003 | Vesely ........................ 623/1.11 |
| 2003/0149476 A1 | * | 8/2003 | Damm et al. ............... 623/2.1 |
| 2003/0163194 A1 | * | 8/2003 | Quijano et al. ............ 623/2.11 |
| 2003/0167089 A1 | * | 9/2003 | Lane .......................... 623/2.14 |
| 2003/0212454 A1 | * | 11/2003 | Scott et al. ................ 623/2.14 |

* cited by examiner

Primary Examiner—Suzette J. Jackson
(74) Attorney, Agent, or Firm—Jones Day (57) ABSTRACT

This invention discloses a percutaneously deliverable heart valve and methods of implantation thereof comprising a valve implantation system to be placed at a body channel of a patient comprising a flexible tissue valve with a plurality of valvular leaflets, each of the leaflets having an in-flow edge, an out-flow edge, and side edges, the plurality of leaflets being sewn together at least a potion of their side edges to form an annulus at about the in-flow edge and a plurality of commissure tissues; an annulus base support secured to the annulus, wherein the annulus base support is collapsible and expandable, and commissural fixation means for securing each of the plurality of commissure tissues onto a wall of the body channel.

24 Claims, 11 Drawing Sheets

PERCUTANEOUSLY DELIVERABLE HEART VALVE AND METHODS OF IMPLANTATION

FIELD OF THE INVENTION

The present invention relates to a prosthetic valve for implantation in a body channel, more particularly, to a percutaneously implantable prosthetic heart valve suitable for replacement of a defect or diseased human heart valve and methods of implantation.

BACKGROUND OF THE INVENTION

Replacement heart valves or heart valve prostheses have been fabricated or manufactured for the last forty years. Such devices have been assembled from a variety of materials. Specifically the materials have been of biologic or artificial nature, generally leading to two distinct categories of the prostheses as biological or mechanical replacement heart valves.

The prosthetic heart valves are fabricated to replace the natural heart valves that, because of disease, congenital malformations, ageing or trauma have become dysfunctional and require repair to their functional elements or partial or complete replacement. Characteristics for a desirable prosthetic heart valve may include hemodynamic performance, thrombogenicity, durability and ease of surgical implantation.

Human heart valves under the conditions of normal physiological functions are passive devices that open under the pressure of blood flow on their leaflets. There are four valves in the heart that serves to direct the flow of blood through all chambers in a forward direction. In general, blood leaves the heart lower chambers in the direction to the rest of the body or to the lungs for required oxygenation, or blood enters the lower chambers from the upper chambers of the heart. Similarly, they close under the pressure exerted on the same leaflet elements when blood flow is retrograde, thus impeding return of blood flow to the chamber it has just left. This, under normal conditions, (that is, when the body is not under physical stresses and the heart is beating at the normal resting state of about 70 beats per minute) equates to the leaflets opening by separation from each other, thereby producing an opening or closing by apposing to each other approximately 38 million times per year. It can be surmised that under stress conditions this may be happening at higher rates, thus increasing the number of separations and appositions, as well as the forces of impact between the leaflets during the closing.

When disease conditions affect the structure of the materials of the components of the valve apparatus, the valve itself will decay, degenerate or disrupt and require repair or replacement to restore proper function necessary for the continuation of life.

The shape of the leaflet and surrounding elements of a valve or a valve apparatus is dependent on the function of the heart. In the case of the atrioventricular valves, otherwise known as mitral (in the left lower chamber of the heart) and tricuspid (in the right ventricle), the valve is part of a continuum that extends from the myocardium or muscular wall of the lower chambers, through the papillary muscles, to which is attached a confluence of tendinous rope-like elements known as *chordae tendinae* that themselves are attached to the edges of differently shaped leaflets which form the flow-allowing and flow-stopping or obstructing elements (leaflets). These leaflets continue and end at a ring-like structure usually known as annulus, that is part of the skeleton of the heart. It is this continuum which should be called an apparatus rather than just valve.

Thus, there is a tricuspid valve apparatus in the right ventricular chamber and more importantly the mitral valve apparatus within the lower left heart chamber or left ventricle, the pumping function of which provides the systemic flow of blood through the aorta, to keep all tissues of the body supplied with oxygenated blood necessary for cellular function and life. Hence during the cardiac cycle, the valves function as part of a unit composed of multiple interrelated parts, including the ventricular and atria walls, the valve leaflets, the fibrous skeleton of the heart at the atrioventricular ring, and the subvalvular apparatus. The subvalvular apparatus includes the papillary muscle within the ventricle, and the chordae tendinae which connect the papillary muscle to the valve leaflets.

Aortic and pulmonary valves have been replaced with simple trileaflet chemically treated biological valves obtained from animals, or bileaflet mechanical valves without extreme deficiencies in valvular or cardiac function. This is not the case when mitral or tricuspid valves are replaced and the necessary involvement of chordae tendinae and muscular element of the chamber wall are not united to function in harmony with the valve leaflets. Those valves used in the aortic position cannot alone replace the mitral valve apparatus without anatomical and functional compromise. The aortic and pulmonary valves are referred to as "semilunar valves" because of the unique appearance of their leaflets, which are shaped somewhat like a half-moon and are more aptly termed "cusps". The aortic and pulmonary valves each have three cusps.

Aortic stenosis is a disease of the aortic valve in the left ventricle of the heart. This aortic valvular orifice can become tightly stenosed, and therefore the blood cannot anymore be freely ejected from the left ventricle. In fact, only a reduced amount of blood can be ejected by the left ventricle which has to markedly increase the ventricular chamber pressure to pass the stenosed aortic orifice. In such aortic diseases, the patients can have syncope, chest pain, and mainly difficulty in breathing. The evolution of such a disease is disastrous when symptoms of cardiac failure appear and many patients die in the year following the first symptoms of the disease.

The only commonly available treatment is the replacement of the stenosed aortic valve by a prosthetic valve via open-heart surgery. U.S. Patent Application publication 2002/0052651 to Myers et al., entire contents of which are incorporated herein by reference, discloses a tubular prosthetic semilunar or atrioventricular heart valve by adding substantially rectangular commissural mounting tabs or pads at the distal end. The commissural mounting tab is generally used for stitching or suturing onto the wall of the body channel.

If surgery is impossible to perform, i.e., if the patient is deemed inoperable or operable only at a too high surgical risk, an alternative possibility is to dilate the valve (that is, an endovascularly deliverable heart valve) with a balloon catheter to enlarge the aortic orifice. Unfortunately, the result is sub-optimal with a high restenosis rate or dysfunction for a conventional stented heart valve.

Aortic stenosis is a very common disease in people above seventy years old and occurs more and more frequently as the subject gets older. Until recently, the implantation of a valve prosthesis for the treatment of aortic stenosis is considered unrealistic to perform since it is deemed difficult to superpose another implantable valve on the distorted stenosed native valve without excising the latter.

Percutaneous Catheter-Based Delivery

Andersen et al. in U.S. Pat. No. 6,168,614, entire contents of which are incorporated herein by reference, discloses a heart valve prosthesis for implantation in the body by use of a catheter. The valve prosthesis is consisted of a support structure with a tissue valve connected to it, wherein the support structure is delivered in a collapsed shape through a blood vessel and secured to a desired valve location with the support structure in the expanded shape. However, the support structure tends to compressively impinge a portion of the leaflets of the tissue valve at the structure struts when the support structure is expanded by an inflatable balloon for positioning endovascularly. The impinged leaflets tend to deteriorate and calcify, making the valve useless.

Andersen et al. in U.S. Pat. No. 5,411,552, No. 5,840,081, and No. 6,168,614, entire contents of which three are incorporated herein by reference, discloses a system for implanting a valve in a body channel comprising a radially collapsible and expandable stent with a valve mounted to it and a catheter for introducing and securing the valve in the body channel. The catheter generally comprises an expandable member about which the cylindrical stent may be positioned together with the valve, fastening means on the expandable member on which the stent may be mounted to the expandable member, and a channel extending through the catheter for injecting a fluid into the expandable member so as to expand the expandable member from a collapsed profile suitable for introduction into the body channel to an expanded profile in which the stent engages the inner wall of the body channel so as to secure the valve therein. It would have been more appropriate to leave the tissue portion of the heart valve alone without any metal impinging from the expandable members.

Letac et al. in U.S. patent application Ser. No. 2001/0007956 and No. 2001/0010017, entire contents of both are incorporated herein by reference, discloses a valve prosthesis for implantation in a body channel comprising a collapsible valvular structure and an expandable frame on which the valvular structure is mounted. However, the expandable frame is made of rigid metal wires or struts that tends to impinge onto the leaflets of the collapsed valvular tissue structure when expanded by an inflatable balloon.

It is one aspect of the present invention to provide a percutaneously deliverable heart valve prosthesis comprising a stentless tissue valve mounted on an annular ring that has a plurality of rivets to endoluminally attaching the commissure tissues onto the inner wall of the body channel after positioning the annular ring in place.

Percutaneous Intercostal Delivery

Various surgical techniques may be used to repair a diseased or damaged valve, including annuloplasty (contracting the valve annulus), quadrangular resection (narrowing the valve leaflets), commissurotomy (cutting the valve commissures to separate the valve leaflets), or decalcification of valve and annulus tissue. Alternatively, the valve may be replaced, by excising the valve leaflets of the natural valve, and securing a replacement valve in the valve position, usually by suturing the replacement valve to the natural valve annulus.

A conventional procedure for approaching the left atrium is by intravascular catheterization from a femoral vein through the cardiac septal which separates the right atrium and the left atrium. In some aspects, this intravascular procedure is not only dangerous and tedious because of long tortuous route, but also limited use because of the catheter size suitable for insertion intravascularly.

Sterman et al. in U.S. Pat. No. 6,283,127, entire contents of which are incorporated herein by reference, discloses a device system and methods facilitating intervention within the heart or great vessels without the need for a median sternotomy or other form of gross thoracotomy, substantially reducing traunia, risk of complication, recovery time, and pain for the patient. Using the device systems and methods of the invention, surgical procedures may be performed through percutaneous penetrations within intercostal spaces of the patient's rib cage, without cutting, removing, or significantly displacing any of the patient's ribs or sternum. The device systems and methods are particularly well adapted for heart valve repair and replacement, facilitating visualization within the patient's thoracic cavity, repair or removal of the patient's natural valve, and, if necessary, attachment of a replacement valve in the natural valve position.

Of particular interest in the present application are techniques for the implantation of an aortic valve that can be retracted or folded inside a delivery system or cannula for delivering through a less invasive intercostal penetration to the desired place, particularly in a left atrium. Thereafter the retracted valve with a supported annulus is released and expanded, followed by securing the commissure tissues of the valve with a plurality of rivets or the same onto the wall of the body channels at a desired anatomical place with a minimally invasive technique.

Most conventional tissue valves are constructed by sewing the leaflets of pig aortic valves to a stent to hold the leaflets in proper position as a stented porcine valve. The tissue valve applicable in the current invention may be constructed by configuring valve leaflets from the pericardial sac of cows or horses and sewing them to an annulus support as a stentless pericardium valve. The annular support may be rigid or slightly flexible and covered with cloth (usually a synthetic material sold under the trademark Dacron™ or Teflon™) for fixation to the patient's native tissue. In one aspect, the annulus base support comprises a cloth cover, wherein the cloth cover is made of polystyrene, polyester, expanded polytetrafluoroethylene, or other biocompatible material. In one embodiment, the porcine, bovine, ovine or equine tissue is chemically treated to alleviate any antigenicity.

The main advantage of tissue valves is that they do not cause blood clots to form as readily as do the mechanical valves, and therefore, the tissue valves do not typically require life-long systemic anticoagulation. Another advantage is that a tissue valve is so flexible that it can be shaped and configured for delivery percutaneously or endoluminally. It is one aspect of the present invention to provide a prosthetic heart valve with the expandable-collapsible support base having flexibility of modifying configuration at the collapsed stage for easy delivery percutaneously.

Therefore, it would be desirable to provide a delivery system for delivering a prosthetic heart valve to a patient's heart configured to be releasably folded inside a lumen of the delivery system through a percutaneous intercostal penetration of a patient's chest or an opening at a carotid artery, jugular vein, subclavian vein, femoral vein, femoral artery and other blood vessel.

SUMMARY OF THE INVENTION

It is one object of the present invention to provide a valve implantation system to be placed at a body channel of a patient comprising: a flexible tissue valve with a plurality of valvular leaflets, each of the leaflets having an in-flow edge, an out-flow edge, and side edges, the plurality of leaflets being sewn together at least a potion of their side edges to form an annulus at about the in-flow edge and a plurality of commissure tissues; an annulus base support secured to the annulus, wherein the annulus base support is collapsible and expandable; and commissural fixation means for securing each of the plurality of commissure tissues onto a wall of the body channel.

In some aspect, the flexible tissue valve of the present invention is categorized as a stentless valve because no stenting is provide to support the leaflet tissue except at the annular base portion adjacent to the leaflet in-flow edges, where the annular base support is provided.

It is another object of the present invention to provide a method of endoluminally delivering and implanting a prosthetic valve at a body channel comprising: providing a valve implantation system, the valve implantation system comprising a flexible tissue valve with a plurality of leaflet commissure tissues and an annulus, wherein the annulus is securely connected to an annulus base support that is configured being collapsible and expandable, and commissural fixation means for securing each of the plurality of leaflet commissure tissues onto a wall of the body channel; passing the flexible tissue valve though the body channel with the annulus base support in a collapsed position, securing the tissue valve to a desired location with the annulus base support in an expanded position; and securing the commissure tissues onto the wall of the body channel by the commissural fixation means In one aspect, the commissural fixation means include valve riveting, stapling, suturing, gluing, tissue welding or the like.

It is still another object of the present invention to provide a method of endoluminally delivering and implanting a prosthetic valve at a body channel comprising: providing a valve implantation system, the valve implantation system comprising a flexible tissue valve with a plurality of leaflet commissure tissues and an annulus, wherein the annulus is securely connected to an annulus base support that is configured being collapsible and expandable, and commissural fixation means for securing each of the plurality of leaflet commissure tissues onto a wall of the body channel; passing the flexible tissue valve though the body channel with the annulus base support in a collapsed position, the flexible tissue valve with the annulus base support being collapsibly held within a delivery apparatus, delivering the tissue valve to a desired location; securing the tissue valve with the annulus base support in an expanded position; and securing the commissure tissues onto the wall of the body channel by the commissural fixation means configured for endoluminally penetrating through the commissure tissues and the wall of the body channel enabling securing the commissure tissues onto the wall.

In some aspect, the delivery means include a catheter, a cannula or the like in still another aspect, the tissue valve prosthesis includes an aortic valve, a mitral valve, a tricuspid valve, a pulmonary valve or a venous valve.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 10, what is shown is an embodiment of a percutaneously deliverable heart valve prosthesis and fixation means thereof. The same principles of percutaneously implantable valves could also apply to implantation of a venous valve, an esophagus valve, ureter valve, a biliary valve, and a valve in the intestines or in the lymphatic systems. While the description sets forth various embodiment specific details, it will be appreciated that the description is illustrative only and should not to be construed in any way as limiting the invention. Furthermore, various applications of the invention, and modifications thereto, which may occur to those who are skilled in the art, are also encompassed by the general concepts described below.

Andersen et al. in U.S. Pat. No. 6,168,614, No. 5,840,081 and No. 5,411,552 discloses a valve prosthesis for implantation in the body by use of a catheter comprising a stent structure made from an expandable cylinder-shaped thread structure comprising several spaced apices struts. The elastically collapsible valve is mounted on the stent at the commissural points of the valve and is secured to the projecting apices. The valve prosthesis can be compressed around the balloon of the balloon catheter and be inserted in the aorta. When the valve prosthesis is placed correctly, the balloon is inflated thereby expanding the stent and wedging it against the wall of the aorta. However, in subsequently animal studies, it is found that the struts impinge into the valvular leaflet tissue when the stent is wedged against the wall of the aorta. The compressed or impinged tissue becomes weak and calcifiable.

Figure 1:
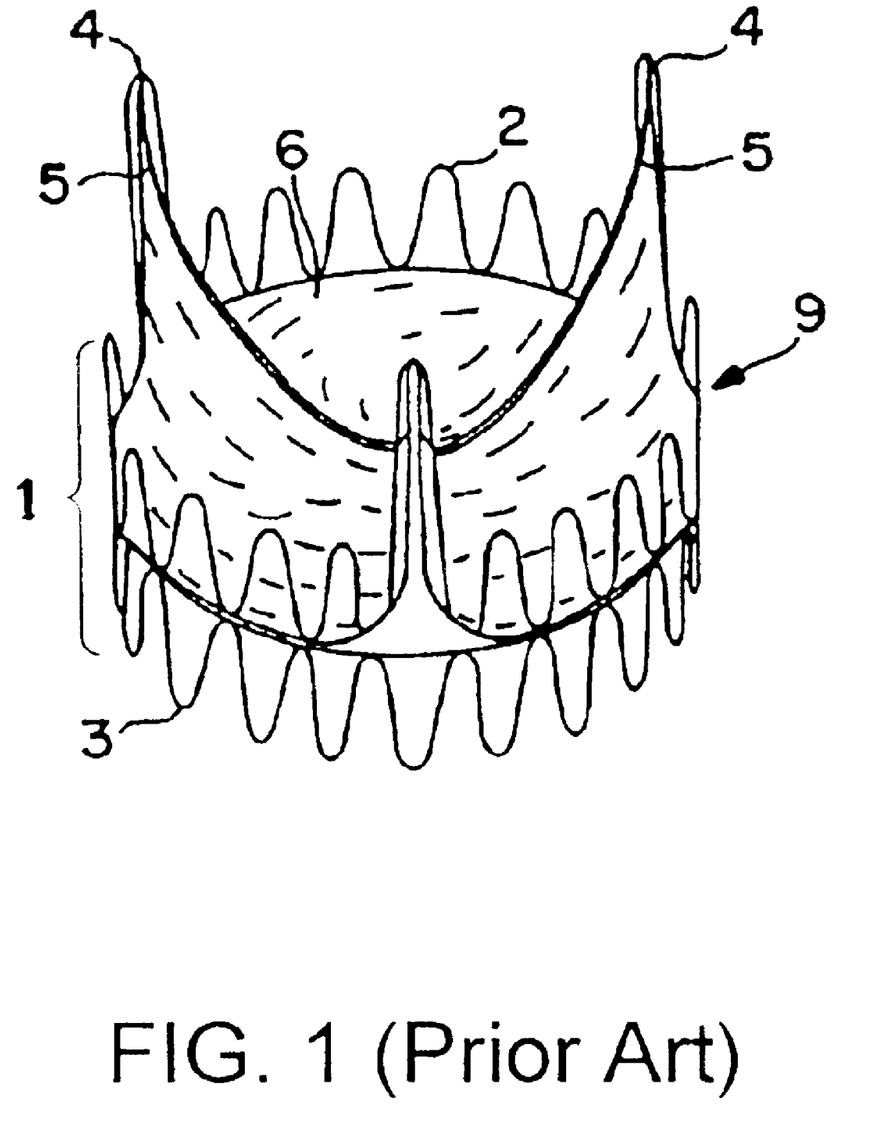
FIG. 1 is a perspective view of a conventional valve prosthesis having a biological valve mounted on a stent structure (prior art).

To better illustrate the structure of a conventional valve prosthesis and the drawbacks, FIG. 1 shows a perspective view of a valve prosthesis example 9 having a biological valve mounted on a stent structure. FIG. 1 shows a stent made by support means in the form of surgical stainless steel wires 2, 3. The wires are folded in several loops. Among them, three loops 4 are elongated and are intended to secure the commissural points 5 from a biological cardiac valve 6 which is mounted in the stent 1. The remaining loops have a shorter height to support the leaflet portion that stays away from the commissural points 5. These loops form a continuous circumferentially expandable section connecting the commissural supports at points 5.

The biological valve 6 in this prior art example is a porcine heart valve mounted in the stent 1. The valve 6 is mounted in the stent by means of a suitable number of sutures or stitches to form the cardiac valve prosthesis 9 shown in FIG. 1 and FIG. 2.

Figure 2:
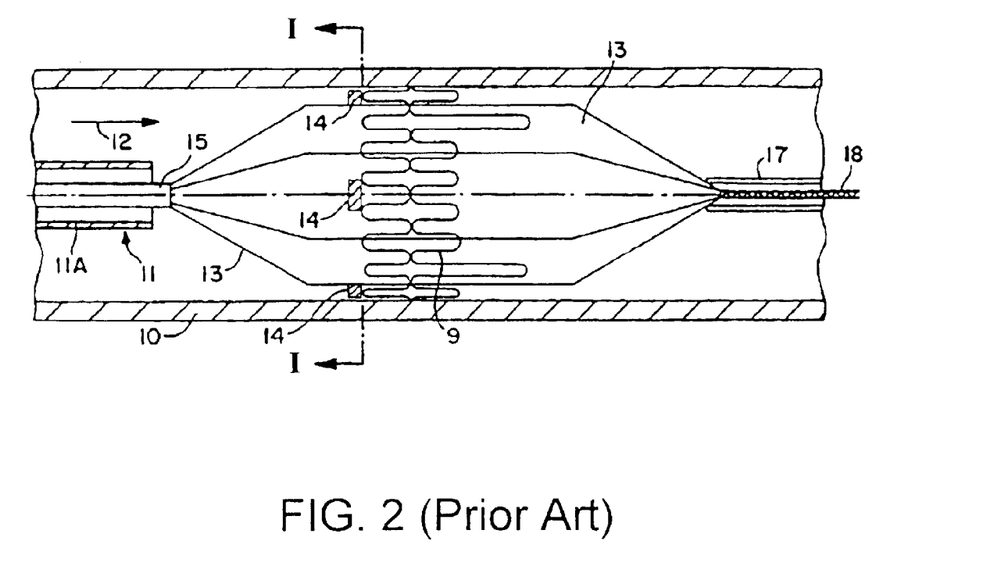
FIG. 2 is a partial view through the aorta illustrating a partially inflated balloon catheter with the stented biological valve prosthesis of FIG. 1 (prior art).

FIG. 2 shows a partial view through the aorta illustrating a partially inflated balloon catheter with the stented biological valve prosthesis of FIG. 1 (prior art). A balloon catheter 11 is introduced in the aorta according to the direction of an arrow 12. In FIG. 2, the balloon means 13 of the balloon catheter is pushed out of the protection cap 11A and is partially inflated through a fluid channel 15, which is connected to an external fluid supply. In one aspect of the example, the balloon means 13 constitutes a tri-sectional balloon upon which the cardiac valve prosthesis 9 is releasably mounted. As shown, the cardiac valve prosthesis 9 is expanded to be in contact with the aorta 10. In some aspect, the balloon catheter 11 comprises a central channel 17 to receive a guide wire 18 which is well known to one of skill in the art for introducing the catheter 11 to an appropriate location. A plurality of beads 14 is provided to make an effective fastening of a valve prosthesis 9 on balloon means 13.

Figure 3:
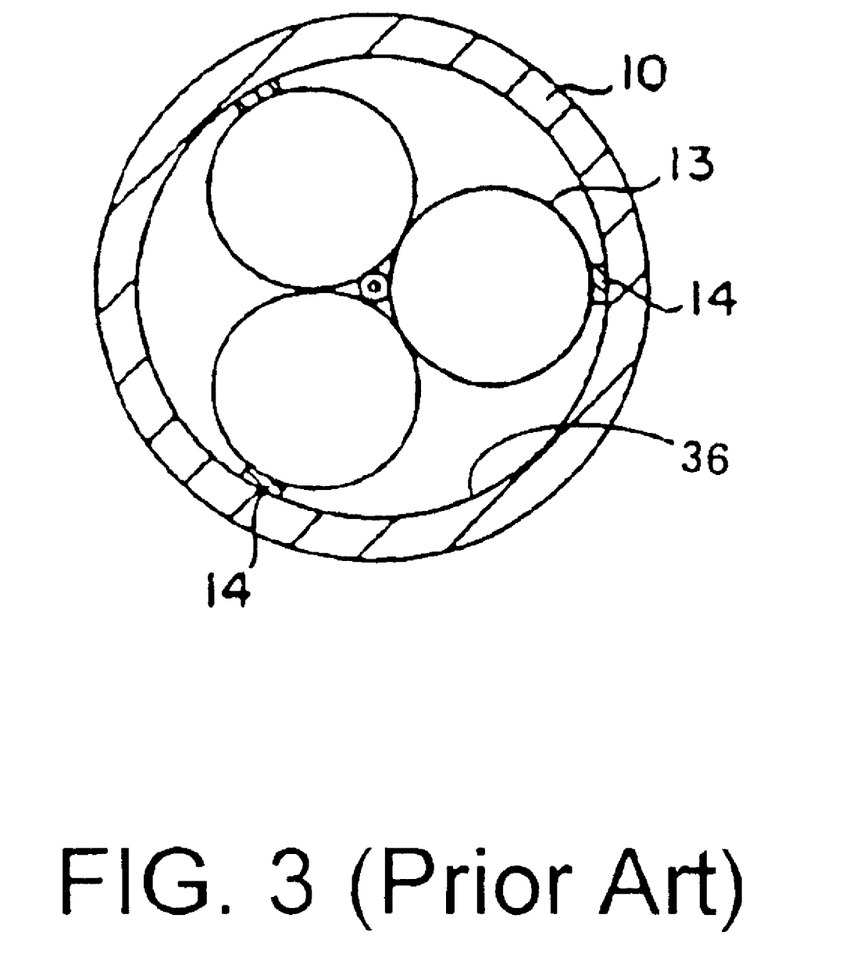
FIG. 3 is a cross section, section I—I of FIG. 2, of the embodiment shown in FIG. 2 (prior art)

FIG. 3 shows a cross section, section I—I of FIG. 2, of the prior art embodiment illustrating the placement of the beads 14 on the tri-sectional balloon means 13. It also demonstrates the drawbacks of impinging the leaflet tissue by the balloon means 13 against the inner wall 36 of the aorta 10. In some aspect of the present invention, it is provided a method for implanting a stentless aortic valve prosthesis comprising a rivet-type fixation means for securing the leaflet commissure tissues 5 onto the vessel wall 36 of a body channel endoluminally.

Letac et al. in U.S. patent application Ser. No. 2001/0007956 and No. 2001/0010017, entire contents of both are incorporated herein by reference, discloses a valve prosthesis for implantation in a body channel comprising a collapsible tissue valve and an expandable stent frame on which the tissue valve is mounted. As discussed above, the Letac et al. valve prosthesis inherently suffers the same undesired drawbacks of the prior art valve prosthesis with respect to the impingement of the leaflet tissue by the balloon means 13 against the inner wall 36 of the aorta 10 through the stent struts or structure of a stented valve. The impinged leaflet tissue tends to deteriorate and calcify, rendering the prosthetic valve useless.

Garrison et al. in U.S. Pat. No. 6,425,916, entire contents of which are incorporated herein by reference, discloses a valve implantation system comprising a valve displacer and a replacement valve prosthesis. The valve displacer and the valve prosthesis are in a collapsed condition during introduction and are expanded to deploy the valve displacer and the valve prosthesis. However, Garrison et al. replacement valve prosthesis comprises a metal stent for supporting the valve tissue and the meshed valve displacer compresses the valve tissue during prosthesis expansion, either activity results in the undesired drawbacks of impinging the leaflet tissue against the wall of the blood vessel by the valve prosthesis expansion means, such as an inflatable balloon. The impinged leaflet tissue tends to deteriorate and calcify.

Figure 4:
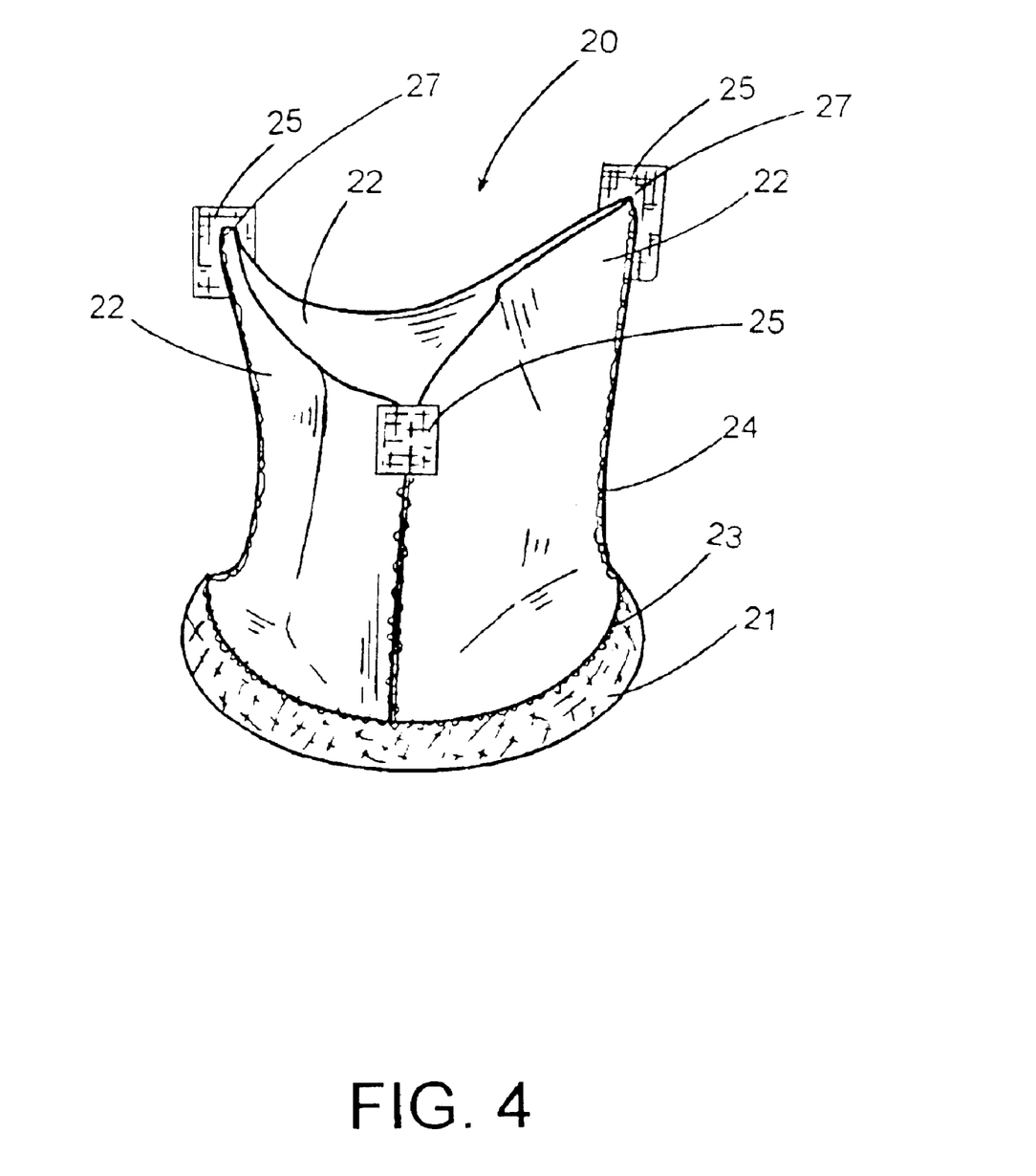
FIG. 4 is a perspective view of a stentless aortic heart valve prosthesis having commissure tissues adapted to secure the commissure tissues onto the inner wall of a blood vessel.

FIG. 4 shows a perspective view of a stentless aortic heart value prosthesis having commissure tissue 27 at about the distal-most commissural points. The "commissure tissue" of the present invention is herein intended to mean the tissue at around the commissural end point of any two leaflets. With reference to FIG. 4, the aortic heart valve prosthesis 20 comprises three leaflets 22 that are cut out of a generally flat, flexible pericardium. The leaflets are secured together by way of sutures 24 to form a tubular aortic valve following the principles "Form Follows Function" disclosed by Cox in U.S. Pat. No. 6,270,526. In some aspect of the present invention, the valve prosthesis further comprises a plurality of tabs 25 mounted at each of the three commissure tissues 27 of the leaflets 22. The leaflets of the tissue valve continue and end at a ring-like structure usually known as annulus whereas the valve prosthesis of the present invention has an annulus base support 21 at the annulus covered with a cloth cover 23 configured and enabling for attaching the annulus base support 21 onto the heart tissue or the wall of the body channel. The cloth cover 23 is secured to the prosthetic tissue leaflet 22 at a position adjacent to the annulus.

Myers et al. in U.S. Patent Application Publication 2002/0052651, entire contents of which are incorporated herein by reference, discloses a stentless prosthetic heart valve, comprising a plurality of leaflets being sewn together along at least a portion of their side edges so as to form a substantially tubular valve structure. However, Myers et al. valve structure is intended for open-chest implantation without the necessary features of percutaneous delivery and implantation, such as a collapsible/expandable base support and means for fixing the commissure tissues onto the aorta wall.

A "stentless prosthetic heart valve" is intended herein to mean a valve prosthesis having an annulus base support but without any stenting structure for the leaflet tissue portion away from the annulus portion. Further, a percutaneously deliverable stentless prosthetic heart valve herein includes a collapsible/expandable base support but without any stenting structure for the leaflet tissue portion other than the annulus. In illustration, the prosthetic heart valves as disclosed by Andersen et al. (in U.S. Pat. No. 5,411,552, U.S. Pat. No. 5,840,081, and U.S. Pat. No. 6,168,614), Letac et al. (in U.S. patent application Ser. No. 2001/0007956 and U.S. patent application No. 2001/0010017), and Garrison et al. (in U.S. Pat. No. 6,425,916) belongs to "stented" prosthetic heart valves.

The cross-sectional diameter of the cylindrical annulus base support 21 is preferred to be about a few millimeters at a collapsed state for prosthesis delivery to about 10 mm or larger at a fully expanded state. The annulus base support 21 is configured and adapted to be sufficiently strong and rigid when the support 21 is fully expanded at about a target implantation location. A collapsible and expandable annulus base support, such as the one used in coronary stenting, is well known to one of skill in the art and does not constitute a part of the present invention. However, to implant the valve prosthesis of the present invention at a valvular annulus, the annulus base support 21 should have adequate hoop strength (that is, the strength in an outwardly radial direction of the circular support structure) to expand the valvular annulus and resist the strong recoil force exerted by the distorted stenosed valve orifice after delivery and expansion step.

In general, the annulus base support along with its unstented tissue leaflets is either self-expandable or could be expanded by an expandable instrument such as an inflatable balloon. The base support 21 may further comprise protrusions, barbs, needles, or other anchoring mechanism for engaging the valve prosthesis to the desired location of a patient. The annulus base support 21 is made of a material selected from a group consisting of polyethylene, polypropylene, polycarbonate, nylon, polytetrafluoroethylene, polyurethane, stainless steel, Nitinol, titanium, polyimide, polyester, shape-memory material, and mixture thereof.

Figure 5:
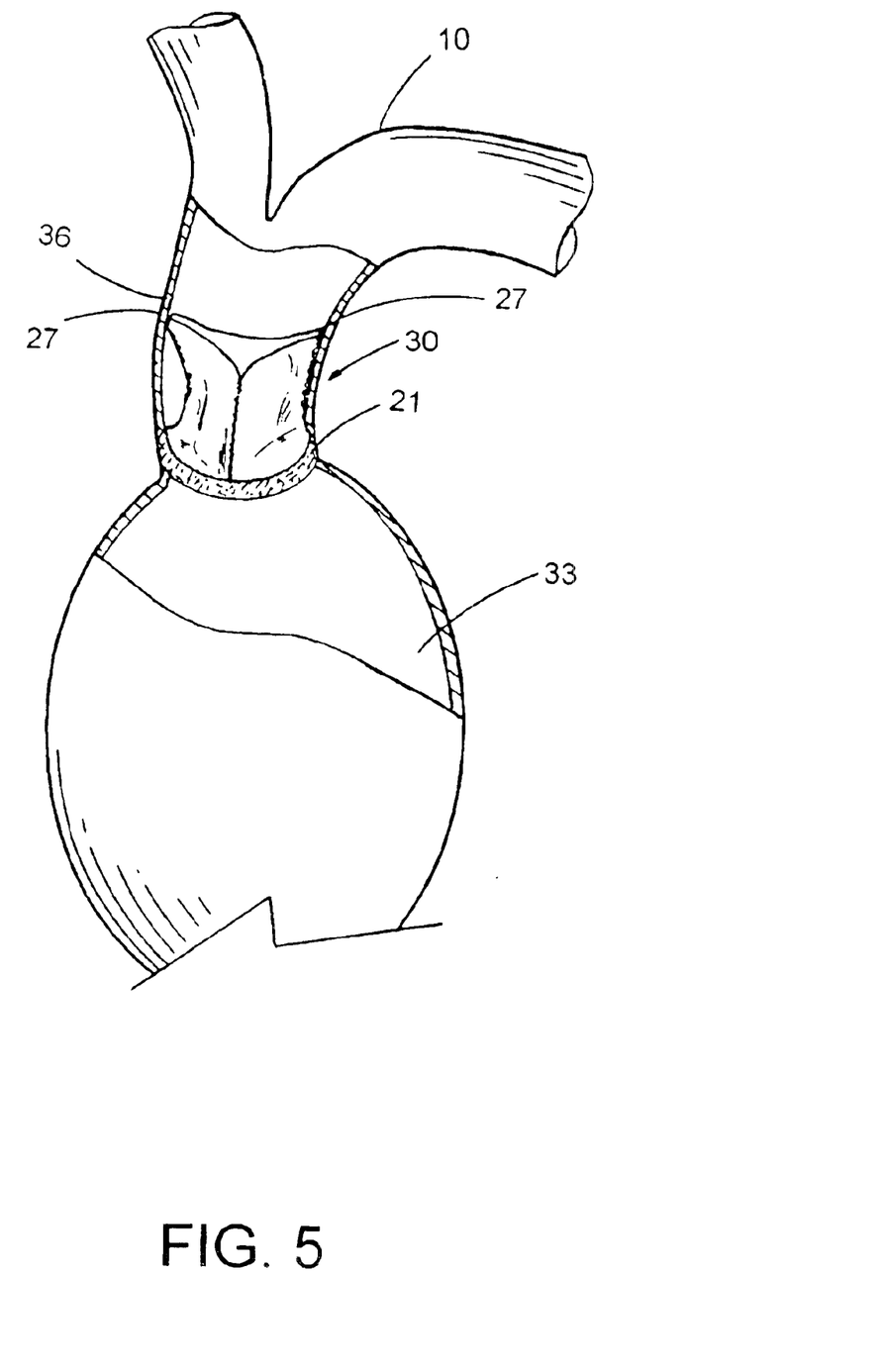
FIG. 5 illustrates a prosthetic aortic heart valve without commissural tabs placed at an anatomical position for prosthetic aortic valve implantation.

FIG. 5 illustrates a prosthetic aortic heart valve 30 without commissural tabs being placed at an anatomical position for prosthetic aortic valve implantation. In operation, the prosthetic heart valve 30 is collapsed and positioned within delivery means and introduced into the aorta area by a percutaneous method or an intercostal penetration method, wherein the delivery means is selected from a group consisting of a delivery catheter, a sheath, a cannula, an applicator, or the like. The valve 30 is deployed out of the delivery means and expanded, if a non self-expanding prosthetic valve is used, being adapted for placing the valve annulus base support 21 at the anatomical valvular position of the heart 33. The distal end 27 of the commissure tissues needs to be secured to the wall 36 of the aorta 10. In the conventional stented valve prosthesis, the tissue leaflets are secured to the "stent" as means for fixation and there is no need for securing the leaflets onto the aorta wall 36. The stent is an integral part of the prior art prosthesis, wherein the stent tends to cause undesired impingement on the leaflet tissue.

In some aspect of the present invention, it is provided a valve implantation system to be placed at a body channel of a patient comprising: a flexible tissue valve with a plurality of valvular leaflets, each of the leaflets having an in-flow edge, an out-flow edge, and side edges, the plurality of leaflets being sewn together at least a potion of their side edges to form an annulus at about the in-flow edge and a plurality of commissure tissues; an annulus base support secured to the annulus, wherein the annulus base support is collapsible and expandable, and commissural fixation means for securing each of the plurality of commissure tissues onto a wall of the body channel.

Figure 6A:
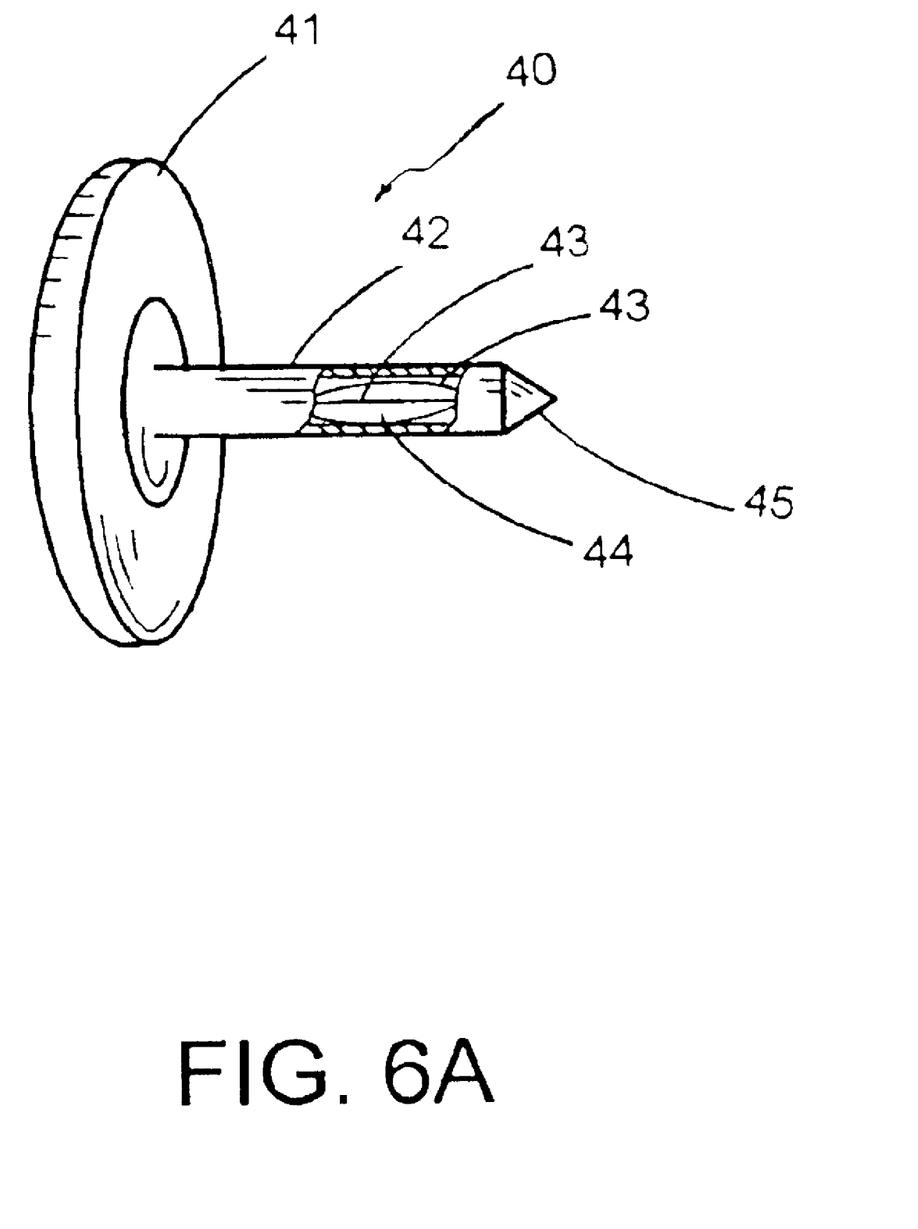
FIG. 6A is a perspective view of one embodiment of valve rivets for securing the leaflet commissure tissues onto the vessel wall endoluminally.

FIG. 6A shows a perspective view of one valve rivet type of commissural fixation means for securing the leaflet commissure tissues onto the vessel wall endoluminally. Other types of commissural fixation means such as stapling, suturing, gluing, welding or the like may work equally well for the intended purposes. In one aspect, the valve rivet 40 has a rivet base 41, a rivet stem 42, and a rivet tip 45 located furthest from the rivet base 41. The rivet tip 45 has generally a sharpened or needle-like distal point for penetrating into a tissue. The distal rivet tip 45 may also be equipped with energy-assisted penetrating means, such as a radiofrequency electrode, microwave antenna, ultrasound transducer or laser. In one aspect, the rivet 40 comprises a plurality of preformed wires 43 compressibly loaded inside a lumen 44 of the rivet stem 42, wherein the preformed wires 43 could be pushed forward (in a deployment step) to expand radially with respect to the stem axis.

Figure 6B:
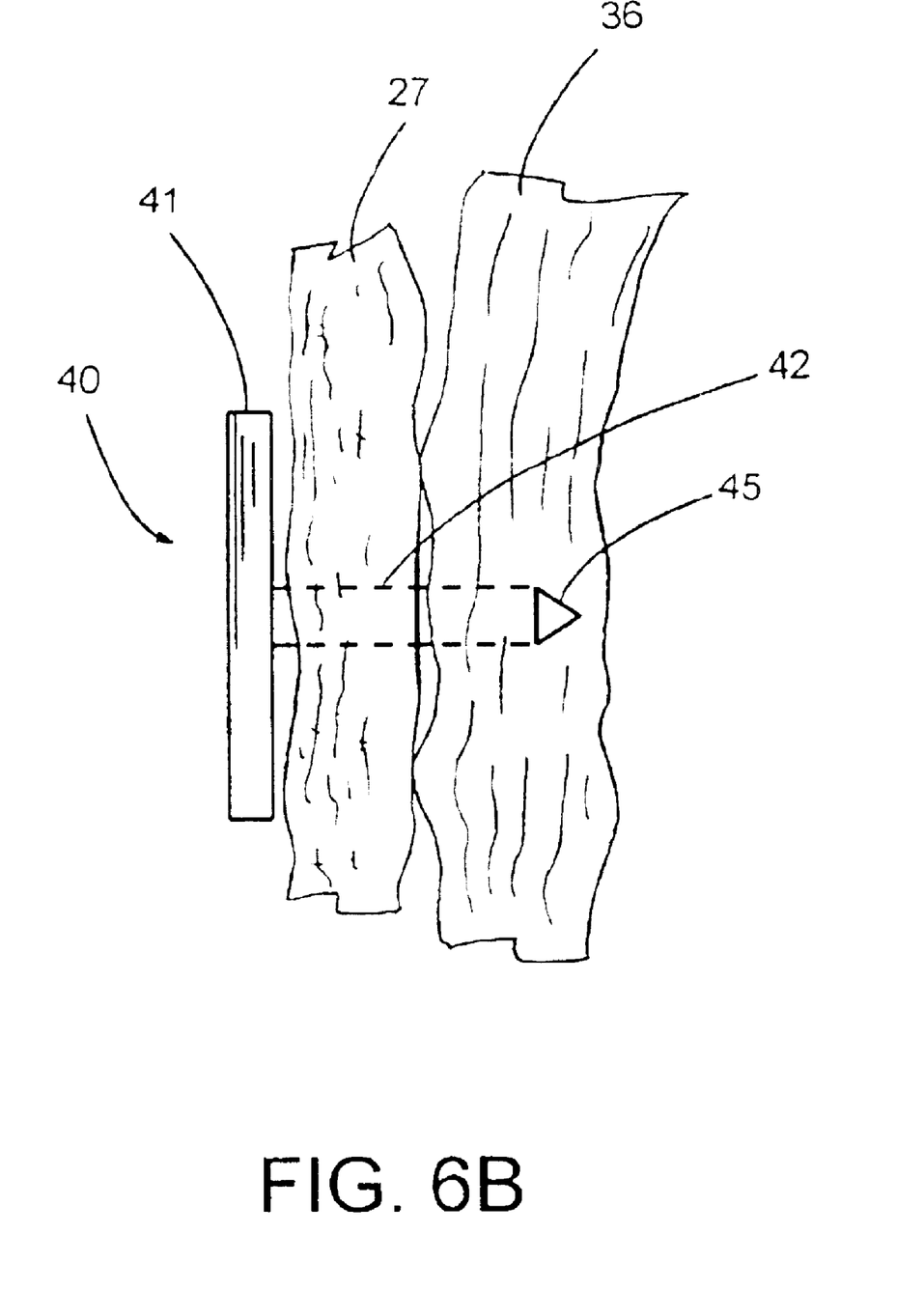
FIG. 6B is a front cross-sectional view of the valve rivet of FIG. 6A at an initial penetrating state for securing a leaflet commissure tissue onto the vessel wall endoluminally

FIG. 6B is a front cross-sectional view of the valve rivet 40 of FIG. 6A at an initial penetrating state for securing a leaflet commissure tissue 27 onto the vessel wall 36 endoluminally. After the tissue valve 30 is delivered and the annulus base support 21 is expanded and secured in place, a fixation apparatus (not shown) having the commissural fixation means (for example, a valve rivet 40 in FIG. 6A or a rivet 50 in FIG. 9) is introduced endoluminally to the prosthetic valve location to place the rivet tip 45 through the commissure tissue 27 into the wall 36 for securing the commissure tissue onto the vessel wall as a part of the valve implantation procedures.

Figure 7:
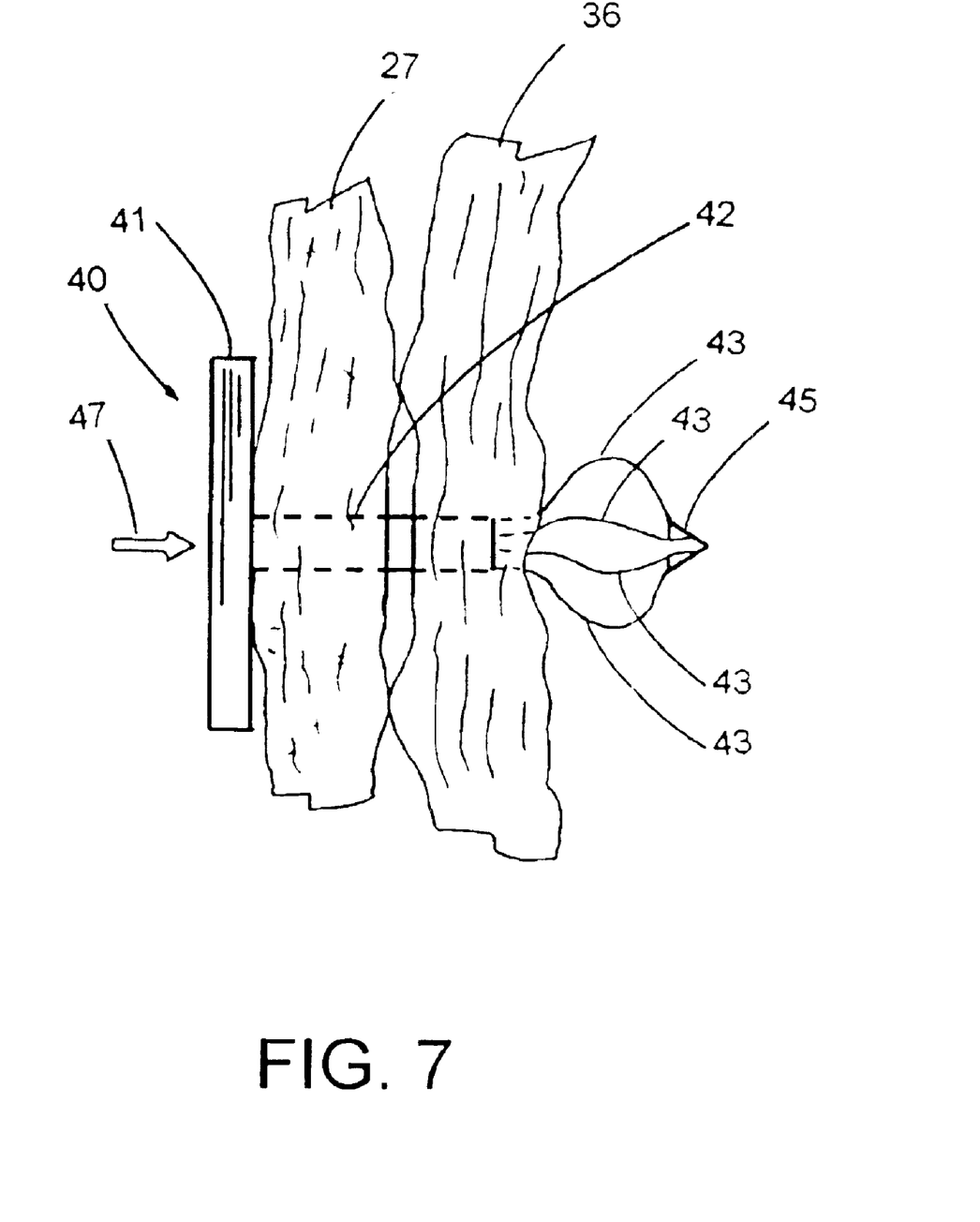
FIG. 7 is a front cross-sectional view of the valve rivet of FIG. 6A at a partially deployed state for securing a leaflet commissure tissue onto the vessel wall endoluminally
Figure 8:
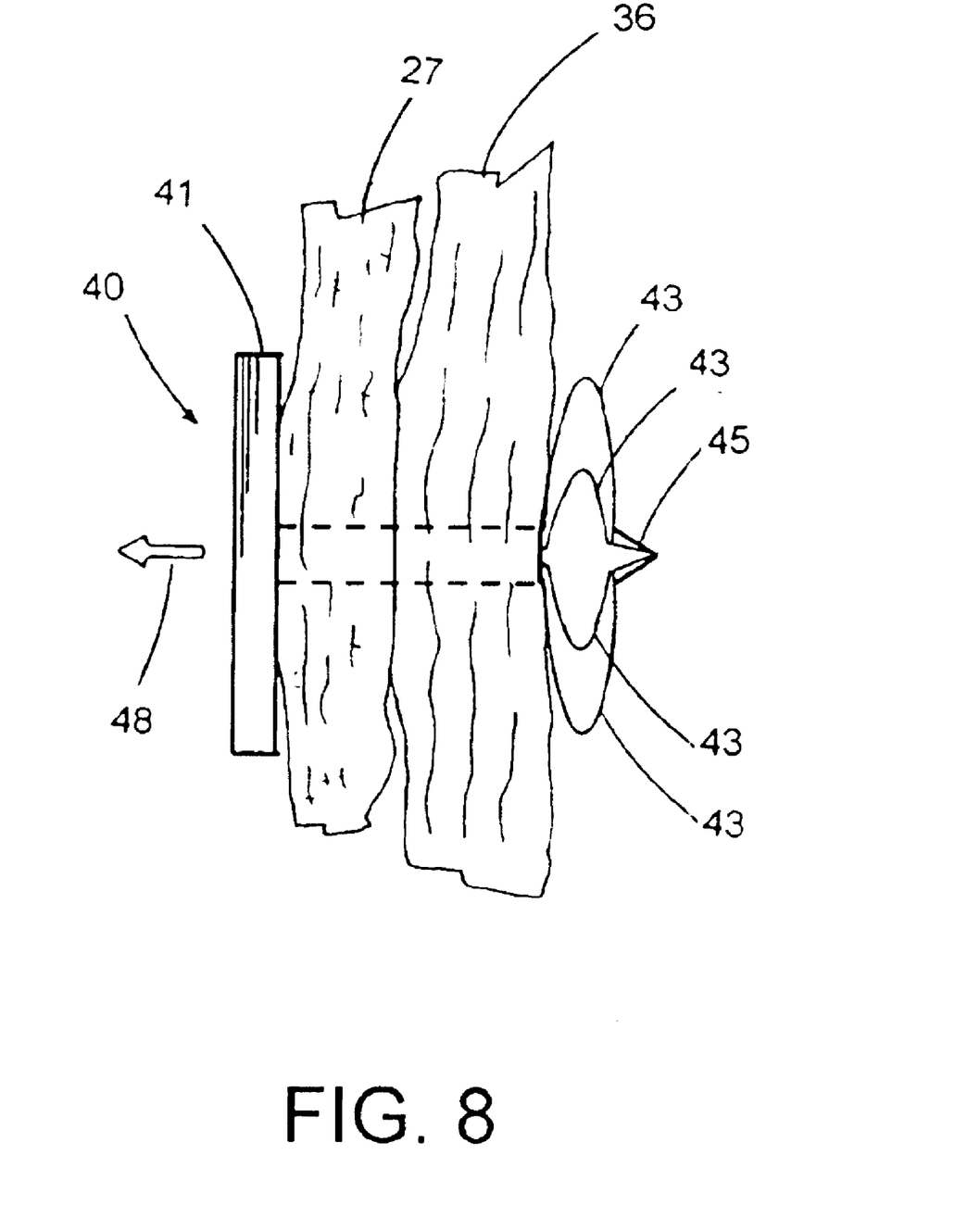
FIG. 8 is a front cross-sectional view of the valve rivet of FIG. 6A at a fully deployed state for firmly securing a leaflet commissure tissue onto the vessel wall endoluminally

In operations, FIG. 7 shows a front cross-sectional view of the valve rivet 40 of FIG. 6A at a stem partially deployed state for securing a leaflet commissure tissue 27 onto the vessel wall 36 endoluminally. After releasing the preformed wires 43 out of the constraint of the rivet stem 42 to beyond the outer surface of the body vessel by a pushing mechanism as shown by an arrow 47, the preformed wires 43 tend to expand radially outwardly to hold the vessel wall 36 in place. Thereafter, the preformed wires 43 may be pulled in an opposite direction (as shown by the arrow 48) to firmly tightening and securing the commissure tissue onto the vessel wall 36 per the rivet principles. FIG. 8 shows a front cross-sectional view of the valve rivet 40 of FIG. 6A at a stem completely deployed state for securing a leaflet commissure tissue 27 onto the vessel wall 36 endoluminally.

Figure 9:
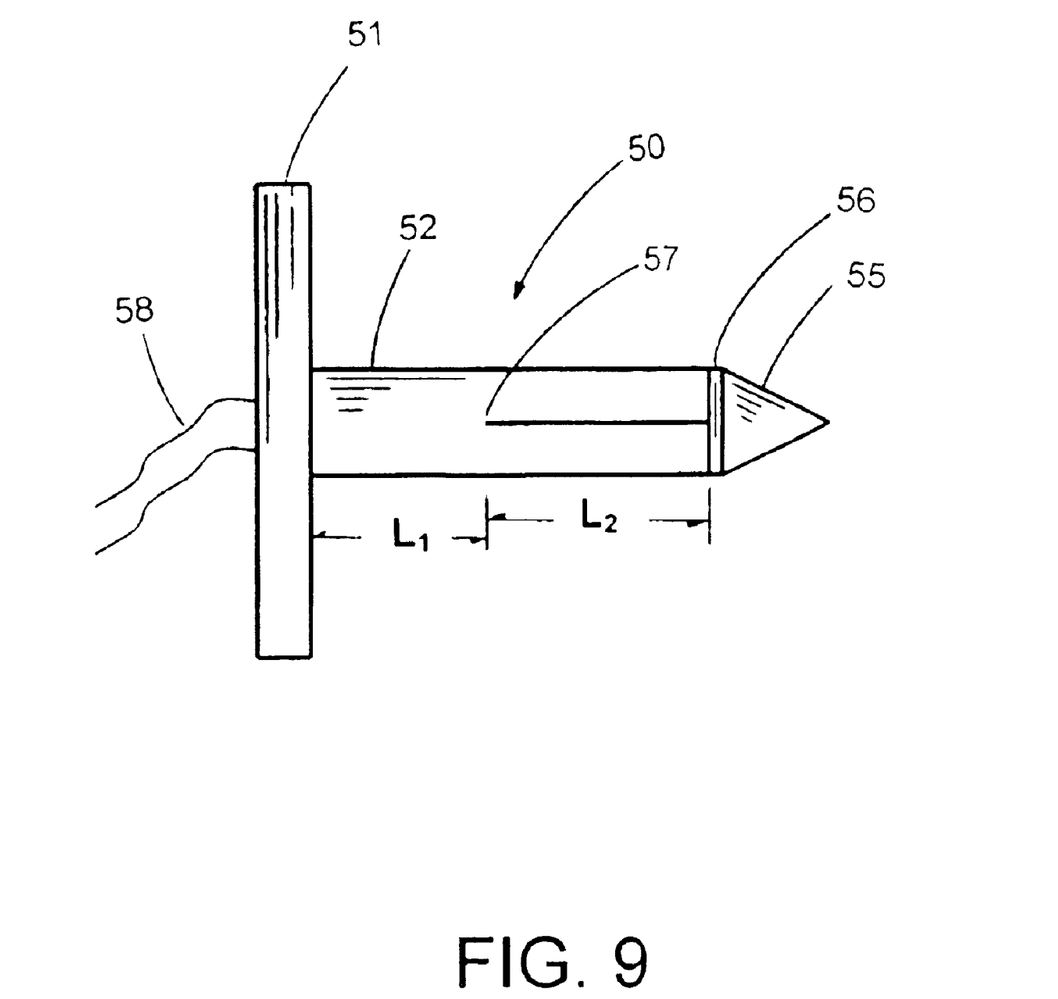
FIG. 9 is a front cross-sectional view of another embodiment of valve rivets for securing the leaflet commissure tissues onto the vessel wall endoluminally
Figure 10:
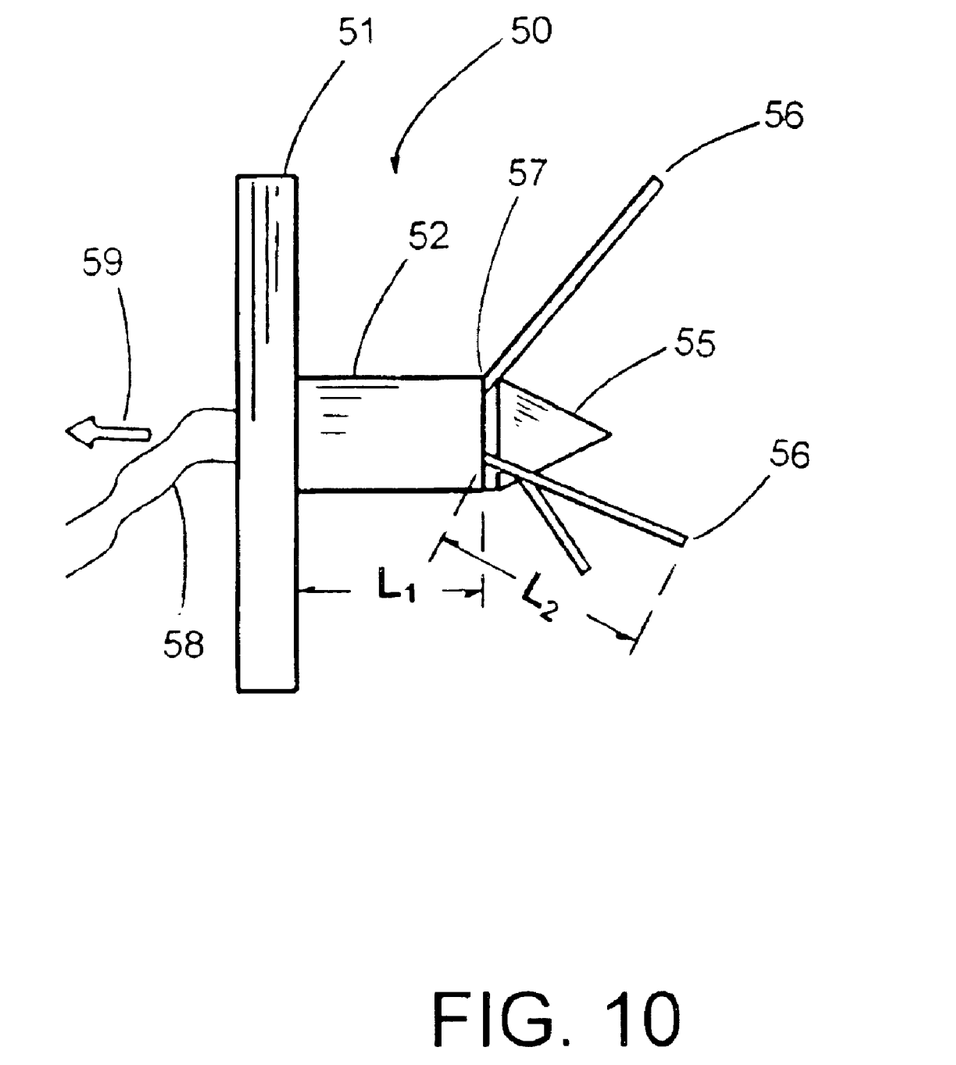
FIG. 10 is a front cross-sectional view of the valve rivet of FIG. 9 at a fully deployed state for firmly securing a leaflet commissure tissue onto the vessel wall endoluminally

FIG. 9 shows a front cross-sectional view of another embodiment of a second valve rivet 50 for securing the leaflet commissure tissues onto the vessel wall endoluminally, while FIG. 10 shows a front cross-sectional view of the second valve rivet 50 of FIG. 9 at a fully deployed state for firmly securing a leaflet commissure tissue onto the vessel wall endoluminally. In some aspect, the second rivet 50 comprises a rivet base member 51, a rivet body 52 and a sharp-ended rivet end 55 located at the furthermost end from the base member 51. The rivet body 52 comprises a plurality of slits extending between the first and the second slit ends 56, 57, wherein the slit-containing portion is designated by $L_2$ while the non slit-containing portion is designated by $L_1$. After passing the rivet end 55 of the second rivet 50 through the commissure tissue and the vessel wall, the rivet end 55 is pulled back by strings 58 as indicated by an arrow 59. The $L_2$ portion of the rivet body 52 will tend to turn outwardly as a consequence of the backward compressing of the rivet end 55 onto the rivet body 52.

In one aspect of the valve implantation system of the present invention, the commissural fixation means comprises a valve rivet configured for endoluminally penetrating through one of the commissure tissues and the wall of the body channel enabling securing the commissure tissue onto the wall. In another aspect, the commissural fixation means comprises a staple. In still another aspect, the commissural fixation means comprises a suture to form a knot at the luminal side of the commissure tissue enabling securing the commissure tissue onto the vessel wall. The fixation means of a rivet, a staple or a suture endoluminally is well known to one of skill in the art, for example, U.S. Pat. No. 6,203,553 to Robertson et al, entire contents of which are incorporated herein by reference, discloses a surgical stapler for securing a prosthetic heart valve within a patient.

In some aspect of the present invention, it is provided a method of endoluminally delivering and implanting a prosthetic valve at a body channel comprising providing a valve implantation system, the valve implantation system comprising a flexible tissue valve with a plurality of leaflet commissure tissues and an annulus, wherein the annulus is securely connected to an annulus base support that is configured being collapsible and expandable, and commissural fixation means for securing each of the plurality of leaflet commissure tissues onto a wall of the body channel; passing the flexible tissue valve though the body channel with the annulus base support in a collapsed position; securing the tissue valve to a desired location with the annulus base support in an expanded position; and securing the commissure tissues onto the wall of the body channel by the commissural fixation means.

In another aspect of the present invention, it is provided a method of endoluminally delivering and implanting a prosthetic valve at a body channel. The method comprises steps of providing a valve implantation system, the valve implantation system comprising a flexible tissue valve with a plurality of leaflet, a plurality of leaflet commissure tissues and an annulus, wherein the annulus is securely connected to an annulus base support that is configured being collapsible and expandable, and commissural fixation means for securing each of the plurality of leaflet commissure tissues onto a wall of the body channel. The method further comprises a step of passing the flexible tissue valve though the body channel with the annulus base support in a collapsed position, the flexible tissue valve with the annulus base support being collapsibly held within a delivery apparatus; a step of delivering the tissue valve to a desired location; a step of securing the tissue valve with the annulus base support in an expanded position; and a step of securing the commissure tissues onto the wall of the body channel by the commissural fixation means configured for endoluminally penetrating through the commissure tissues and the wall of the body channel enabling securing the commissure tissues onto the wall.

In one aspect, the delivery apparatus may comprise a catheter, wherein the catheter passes through an opening of the body vessel, such as an incision at a carotid artery, a jugular vein, a subdlavian vein, a femoral artery, a femoral vein, or any body vessel. In another embodiment, the delivery apparatus may comprise a cannula, the cannula passing through a percutaneous intercostal penetration.

The percutaneously deliverable heart valve prosthesis of the present invention comprises a flexible tissue heart valve with a plurality of valvular leaflets attached to the annulus base support, while the remaining portion of the tissue valve is not supported or stented. The flexible tissue valve may be a porcine valve or a valve fabricated from pericardium tissue selected from a group consisting of equine, bovine, porcine, and ovine. In one aspect of the present invention, the porcine valve is procured from a genetically modified porcine, wherein the procured porcine valve is with little rejection when transplanted. The flexible tissue heart valve may further be chemically treated to reduce antigenicity of the tissue, wherein the chemical is selected from a group consisting of glutaraldehyde, formaldehyde, dialdehyde starch, polyepoxy compounds, and mixture thereof.

It is one object of the present invention to provide an expandable-collapsible heart valve prosthesis to replace a diseased valve of a patient. The diseased valve to be replaced may be selected from a group consisting of an aortic valve, a pulmonary valve, a mitral valve, a tricuspid valve, and a venous valve.

The delivery apparatus may be made from plastic material, metal or composite material. In one embodiment, the delivery apparatus may be made of the material selected from the group consisting of polyethylene, polypropylene, polycarbonate, nylon, polytetrafluoroethylene, polyurethane, stainless steel, Nitinol, titanium, polyimide, polyester, and the like.

In some aspect of operations, a delivery apparatus of the present invention may be deployed through an intercostal penetration. The delivery apparatus may be introduced through a cannula or trocar positioned in one of percutaneous intercostal penetrations, the cannula or trocar having a proximal end disposed outside of the patient and a distal end disposed within the chest. The delivery means through a percutaneous intercostal penetration is well known to one who is skilled in the art.

From the foregoing description, it should now be appreciated that a percutaneously deliverable heart valve prosthesis suitable for replacement of a diseased human heart valve and implantation means thereof have been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A method of endoluminally delivering and implanting a prosthetic valve at a body channel comprising:

providing a valve implantation system, the valve implantation system comprising a flexible tissue valve with a plurality of leaflet commissure tissues and an annulus, wherein the annulus is securely connected to an annulus base support that is configured being collapsible and expandable, and commissural fixation means for securing each of the plurality of leaflet commissure tissues onto a wall of the body channel;

passing the flexible tissue valve though the body channel with the annulus base support in a collapsed position;

securing the tissue valve to a desired location with the annulus base support in an expanded position; and securing the commissure tissues onto the wall of the body channel by said commissural fixation means, wherein the step of securing the commissure tissues is carried out by a valve rivet having a plurality of preformed wires configured for endoluminally penetrating through the commissure tissue and the wall of the body channel and enabling securing said commissure tissue onto said wall;

wherein the step of securing the commissure tissues with a valve rivet further comprises the steps of pushing the valve rivet to release and expand a plurality of preformed wires radially outwardly and pulling the valve rivet to compress and expand the preformed wires to secure the commissure tissues to the wall of the body channel.

2. The method of claim 1, wherein the step of securing the commissure tissues is carried out by a valve rivet configured for endoluminally penetrating through the commissure tissue and the wall of the body channel enabling securing said commissure tissue onto said wall.

3. The method of claim 1, wherein the step of securing the commissure tissues is carried out by a suture configured for endoluminally passing through the commissure tissue and the wall of the body channel to form a knot enabling securing said commissure tissue onto said wall.

4. The method of claim 1, wherein the step of securing the commissure tissues is carried out by a staple configured for endoluminally penetrating through the commissure tissue and the wall of the body channel enabling securing said commissure tissue onto said wall.

5. The method of claim 1, wherein the flexible tissue valve is a porcine valve.

6. The method of claim 1, wherein the flexible tissue valve further comprises a plurality of leaflets, said leaflets being made of pericardium tissue selected from a group consisting of equine, bovine, porcine, and ovine.

7. The method of claim 1, wherein the flexible tissue valve is chemically treated with a chemical to reduce antigenicity, wherein the chemical is selected from a group consisting of glutaraldehyde, formaldehyde, dialdehyde starch, polyepoxy compounds, and mixture thereof.

8. The method of claim 1, wherein the flexible tissue valve is an aortic valve.

9. The method of claim 1, wherein the flexible tissue valve is a mitral valve.

10. The method of claim 1, wherein the flexible tissue valve is a tricuspid valve.

11. The method of claim 1, wherein the flexible tissue valve is a pulmonary valve.

12. A method of endoluminally delivering and implanting a prosthetic valve at a body channel comprising:

providing a valve implantation system, the valve implantation system comprising a flexible tissue valve with a plurality of leaflet commissure tissues and an annulus, wherein the annulus is securely connected to an annulus base support that is configured being collapsible and expandable, and commissural fixation means for securing each of the plurality of leaflet commissure tissues onto a wall of the body channel;

passing the flexible tissue valve though the body channel with the annulus base support in a collapsed position, said flexible tissue valve with the annulus base support being collapsibly held within a delivery apparatus;

delivering the tissue valve to a desired location;

securing the tissue valve with the annulus base support in an expanded position; and securing the commissure tissues onto the wall of the body channel by said commissural fixation means configured for endoluminally penetrating through the commissure tissues and the wall of the body channel enabling securing said commissure tissues onto said wall;

wherein the step of securing the commissure tissues is carried out by a valve rivet having a plurality of preformed wires configured for endoluminally penetrating through the commissure tissue and the wall of the body channel and enabling securing said commissure tissue onto said wall, wherein the step of securing the commissure tissues with a valve rivet further comprises the steps of pushing the valve rivet to release and expand a plurality of preformed wires radially outwardly and pulling the valve rivet to compress and expand the preformed wires to secure the commissure tissues to the wall of the body channel.

13. The method of claim 12, wherein the delivery apparatus comprises a catheter.

14. The method of claim 13, wherein the delivery step is carried out with said catheter through an opening of a body vessel selected from a group consisting of a carotid artery, a jugular vein, a subclavian vein, a femoral artery, and a femoral artery.

15. The method of claim 12, wherein the delivery apparatus comprises a cannula.

16. The method of claim 15, wherein the delivery step is carried out with said cannula through a percutaneous intercostal penetration.

17. The method of claim 14, wherein the step of securing the tissue valve with the annulus base support in the expanded position is carried out by an inflatable balloon on the catheter.

18. The method of claim 17, wherein the balloon is selected from a group consisting of compliant material, non-compliant material, and semi compliant material.

19. The method of claim 12, wherein the commissural fixation means comprises a suture configured for endoluminally penetrating through one of the commissure tissues and the wall of the body channel to form a knot enabling securing said commissure tissue onto said wall.

20. The method of claim 12, wherein the commissural fixation means comprises a staple configured for endoluminally penetrating through one of the commissure tissues and the wall of the body channel enabling securing said commissure tissue onto said wall.

21. The method of claim 12, wherein the commissural fixation means comprises a valve rivet configured for endoluminally penetrating through one of the commissure tissues and the wall of the body channel enabling securing said commissure tissue onto said wall.

22. The method of claim 12, wherein the flexible tissue valve is selected from a group consisting of an aortic valve, a mitral valve, a tricuspid valve and a pulmonary valve.

23. The method of claim 12, wherein the flexible tissue valve further comprises a plurality of leadflets, said leaflets being made of pericardium tissue selected from a group consisting of equine, bovine, porcine, and ovine.

24. The method of claim 12, wherein the flexible tissue valve is chemically treated with a chemical to reduce antigenicity, wherein the chemical is selected from a group consisting of glutaraldehyde, formaldehyde, dialdehyde starch, polyepoxy compounds, and mixture thereof.

* * * * *